United States Patent
Aylsworth et al.

(10) Patent No.: US 7,114,497 B2
(45) Date of Patent: Oct. 3, 2006

(54) METHOD AND SYSTEM OF INDIVIDUALLY CONTROLLING AIRWAY PRESSURE OF A PATIENT'S NARES

(75) Inventors: Alonzo C. Aylsworth, Wildwood, MO (US); Lawrence C. Spector, Austin, TX (US)

(73) Assignee: Acoba, LLC, Chesterfield, MO (US)

( * ) Notice: Subject to any disclaimer, the term of this patent is extended or adjusted under 35 U.S.C. 154(b) by 260 days.

(21) Appl. No.: 10/851,952

(22) Filed: May 21, 2004

(65) Prior Publication Data
US 2005/0011523 A1 Jan. 20, 2005

Related U.S. Application Data
(60) Provisional application No. 60/488,615, filed on Jul. 18, 2003.

(51) Int. Cl.
*A61M 16/00* (2006.01)
*A62B 7/00* (2006.01)

(52) U.S. Cl. .............................. 128/204.18; 128/207.18; 128/204.23; 128/204.21; 128/204.26; 128/204.25

(58) Field of Classification Search ............ 128/203.22, 128/204.12, 207.18, 204.21, 204.23, 204.26; 600/538, 532, 529
See application file for complete search history.

(56) References Cited

U.S. PATENT DOCUMENTS

| | | | |
|---|---|---|---|
| 4,922,900 A | 5/1990 | Kiske et al. | |
| 5,117,819 A | 6/1992 | Servidio et al. | |
| 5,148,802 A | 9/1992 | Sanders et al. | |
| 5,161,525 A | 11/1992 | Kimm et al. | |
| 5,239,995 A | 8/1993 | Estes et al. | |
| 5,269,296 A | 12/1993 | Landis | |
| 5,313,937 A | 5/1994 | Zdrojkowski | |
| 5,433,193 A | 7/1995 | Sanders et al. | |
| 5,458,137 A | 10/1995 | Axe et al. | |
| 5,477,852 A | 12/1995 | Landis et al. | |
| 5,492,113 A | 2/1996 | Estes et al. | |
| 5,522,382 A | 6/1996 | Sullivan et al. | |
| RE35,295 E | 7/1996 | Estes et al. | |
| 5,535,738 A | 7/1996 | Estes et al. | |
| 5,537,997 A | 7/1996 | Mechlenburg et al. | |
| 5,540,219 A * | 7/1996 | Mechlenburg et al. . | 128/204.23 |
| 5,551,418 A | 9/1996 | Estes et al. | |
| RE35,339 E | 10/1996 | Rapoport | |
| 5,645,054 A | 7/1997 | Cotner et al. | |
| 5,655,522 A | 8/1997 | Mechlenburg et al. | |
| 5,657,752 A | 8/1997 | Landis et al. | |
| 5,682,878 A | 11/1997 | Ogden | |
| 5,685,296 A | 11/1997 | Zdrojkowski et al. | |
| 5,687,715 A | 11/1997 | Landis et al. | |
| 5,740,795 A | 4/1998 | Brydon | |
| 5,794,614 A * | 8/1998 | Gruenke et al. ........ | 128/204.21 |
| 5,794,615 A | 8/1998 | Estes | |
| 5,803,065 A | 9/1998 | Zdrojkowski et al. | |
| 5,803,066 A | 9/1998 | Rapoport et al. | |
| 5,891,023 A | 4/1999 | Lynn | |
| 5,901,704 A | 5/1999 | Estes et al. | |
| 5,904,141 A | 5/1999 | Estes et al. | |
| 5,937,855 A | 8/1999 | Zdrojkowski et al. | |
| 5,957,133 A | 9/1999 | Hart | |
| 5,970,975 A | 10/1999 | Estes et al. | |
| 6,029,664 A | 2/2000 | Zdrojkowski et al. | |

(Continued)

*Primary Examiner*—Henry Bennett
*Assistant Examiner*—Shumaya B Ali
(74) *Attorney, Agent, or Firm*—Mark E. Scott; Conley Rose, P.C.

(57) ABSTRACT

A method and system of individually controlling positive airway pressure of a patient's nares. Some exemplary embodiments may be a method comprising applying therapeutic gas pressure within a first naris of a patient during respiration, and applying therapeutic gas pressure within a second naris of the patient during the respiration. The therapeutic gas pressures applied to each naris are different.

56 Claims, 5 Drawing Sheets

U.S. PATENT DOCUMENTS

| | | |
|---|---|---|
| 6,041,780 A | 3/2000 | Richard et al. |
| 6,085,747 A | 7/2000 | Axe et al. |
| 6,105,575 A | 8/2000 | Estes et al. |
| 6,112,745 A | 9/2000 | Lang |
| 6,138,675 A | 10/2000 | Berthon-Jones |
| 6,152,129 A | 11/2000 | Berthon-Jones |
| 6,182,657 B1 | 2/2001 | Brydon et al. |
| 6,213,119 B1 | 4/2001 | Brydon et al. |
| 6,223,064 B1 | 4/2001 | Lynn et al. |
| 6,237,593 B1 | 5/2001 | Brydon |
| 6,240,921 B1 | 6/2001 | Brydon et al. |
| 6,253,764 B1 | 7/2001 | Calluaud |
| 6,253,766 B1 | 7/2001 | Niles et al. |
| 6,279,569 B1 | 8/2001 | Berthon-Jones |
| 6,299,581 B1 | 10/2001 | Rapoport et al. |
| 6,302,105 B1 | 10/2001 | Wickham et al. |
| 6,305,374 B1 | 10/2001 | Zdrojkowski et al. |
| 6,318,365 B1 | 11/2001 | Vogele et al. |
| 6,328,753 B1 | 12/2001 | Zammit |
| 6,332,463 B1 | 12/2001 | Farrugia et al. |
| 6,342,039 B1 | 1/2002 | Lynn et al. |
| 6,342,040 B1 | 1/2002 | Starr et al. |
| 6,345,619 B1 | 2/2002 | Finn |
| 6,363,933 B1 | 4/2002 | Berthon-Jones |
| 6,367,474 B1 | 4/2002 | Berthon-Jones et al. |
| 6,397,841 B1 | 6/2002 | Kenyon et al. |
| 6,398,739 B1 | 6/2002 | Sullivan et al. |
| 6,401,713 B1 | 6/2002 | Hill et al. |
| 6,427,689 B1 | 8/2002 | Estes et al. |
| 6,484,719 B1 | 11/2002 | Berthon-Jones |
| 6,502,572 B1 | 1/2003 | Berthon-Jones et al. |
| 6,526,974 B1 | 3/2003 | Brydon et al. |
| 6,530,372 B1 | 3/2003 | Madaus et al. |
| 6,532,956 B1 * | 3/2003 | Hill ........................ 128/204.18 |
| 6,532,960 B1 | 3/2003 | Yurko |
| 6,539,940 B1 | 4/2003 | Zdrojkowski et al. |
| 6,553,992 B1 | 4/2003 | Berthon-Jones et al. |
| 6,575,163 B1 | 6/2003 | Berthon-Jones |
| 6,588,422 B1 | 7/2003 | Berthon-Jones et al. |
| 6,591,834 B1 | 7/2003 | Colla et al. |
| 6,609,517 B1 | 8/2003 | Estes et al. |
| 6,622,724 B1 * | 9/2003 | Truitt et al. ............ 128/204.18 |
| 6,626,174 B1 | 9/2003 | Genger et al. |
| 6,626,176 B1 | 9/2003 | Madaus et al. |
| 6,629,527 B1 | 10/2003 | Estes et al. |
| 6,635,021 B1 | 10/2003 | Sullivan et al. |
| 6,640,806 B1 | 11/2003 | Yurko |
| 6,659,101 B1 | 12/2003 | Berthon-Jones |
| 6,705,315 B1 | 3/2004 | Sullivan et al. |
| 6,752,151 B1 * | 6/2004 | Hill ........................ 128/204.18 |
| 2002/0029004 A1 * | 3/2002 | Starr et al. .................. 600/538 |
| 2004/0074492 A1 | 4/2004 | Berthon-Jones |

* cited by examiner

METHOD AND SYSTEM OF INDIVIDUALLY CONTROLLING AIRWAY PRESSURE OF A PATIENT'S NARES

CROSS-REFERENCE TO RELATED APPLICATIONS

This specification claims the benefit of the provisional application Ser. No. 60/488,615 filed Jul. 18, 2003, titled, "Method And System For Controlling Therapeutic Gas Flow To Each Naris Of A Patient In Positive Airway Pressure Applications," which application is incorporated by reference herein as if reproduced in full below.

STATEMENT REGARDING FEDERALLY SPONSORED RESEARCH OR DEVELOPMENT

Not applicable.

BACKGROUND OF THE INVENTION

1. Field of the Invention

Embodiments of the present invention are directed to positive airway pressure devices and methods, for example continuous positive airway pressure (CPAP) devices. More particularly, embodiments of the invention are directed to positive airway pressure devices and methods where the flow and/or pressure through each nostril or naris and the patient's mouth may be individually controlled.

2. Background of the Invention

Sleep disordered breathing is common throughout the population. Some sleep disorders may be attributable to disorders of the respiratory tract. Sleep apnea may be a disorder where a person temporarily stops breathing during sleep. A hypopnea may be a period of time where a person's breathing becomes abnormally slow or shallow. In some cases, a hypopnea may precede an apnea event.

Although hypopneas and apneas may have multiple causes, one trigger for these type events may be full or partial blockages in the respiratory tract. In particular, in some patients the larynx may collapse due to forces of gravity and/or due to forces associated with lower pressure in the larynx than outside the body. A collapse of the pharynx, larynx, upper airway or other soft tissue in the respiratory tract may thus cause a full or partial blockage, which may lead to a hypopnea or apnea event.

One method to counter collapse of the larynx may be the application of positive airway pressure, possibly by using a CPAP machine. This may be accomplished in the related art by placing a mask over at least the patient's nose, and providing within the mask a pressure communicated to the pharynx, larynx, or upper airway. The pressure within the pharynx, larynx, or upper airway may be greater than the pressure outside the body, thus splinting the airway open.

CPAP machines are concerned only with the pressure of the gas supplied at the nostrils of the patient. However, gases flowing from a region of high pressure to a region of low pressure will take the path of least resistance. Thus, breathable gases provided to a patient in the related art may flow only or predominantly through an open nostril or naris. Forcing or allowing all the gas flow to move through a single naris may cause patient discomfort, both because of the volume of the flow and because of the drying effects experienced by the naris through which the gas moves. The flow problem may be exacerbated by a patient attempting to mouth breath while using a CPAP machine.

SUMMARY OF SOME OF THE PREFERRED EMBODIMENTS

The problems noted above are solved in large part by a method and system of individually controlling positive airway pressure of a patient's nares. Some exemplary embodiments may be a method comprising applying therapeutic gas pressure within a first naris of a patient during respiration, and applying therapeutic gas pressure within a second naris of the patient during the respiration. The therapeutic gas pressures applied to each naris are different.

Other exemplary embodiments may be a system comprising a first blower having an outlet port fluidly coupled to a first pressure transducer (wherein the first blower operatively couples to a first naris of a patient), and a second blower having an outlet port fluidly coupled to a second pressure transducer (wherein the second blower operatively couples to a second naris of the patient).

Yet further exemplary embodiments may be a method comprising applying a therapeutic gas flow into a first naris of a patient during an inhalation (the therapeutic gas flow comprising substantially all the gas inspired through the first naris during the inhalation), and applying a therapeutic gas flow into a second naris of a patient during the inhalation (the therapeutic gas flow comprising substantially all the gas inspired through the second naris during the inhalation). The therapeutic gas flow into each naris is achieved by differing applied pressures within each naris.

Other exemplary embodiments may be a system comprising a first blower fluidly coupled to an outlet port through a first flow sensor (wherein the first blower and first flow sensor operatively couple to a first naris of a patient and provide substantially all the gas inspired through the first naris during an inhalation), and a second blower fluidly coupled to an outlet port through a second flow sensor (wherein the second blower and second flow sensor operatively couple to a second naris of the patient and provide substantially all the gas inspired through the second naris during the inhalation). A pressure applied by the first blower to the first naris to achieve a desired gas flow is different that a pressure applied by the second blower to the second naris to achieve a desired gas flow.

Yet further exemplary embodiments may be a method comprising selectively supplying positive airway pressure to one or both of a patient's nares during an inhalation, and supplying positive airway pressure to the patient's mouth during the inhalation.

Other exemplary embodiments may be a system comprising a first blower fluidly coupled to an outlet port (wherein the first blower operatively couples to a first naris of a patient and provides substantially all the gas inspired through the first naris during an inhalation), and a second blower fluidly coupled to an outlet port, wherein the second blower operatively couples to a mouth of the patient and provides substantially all the gas inspired through the mouth during the inhalation.

Yet further exemplary embodiments may be a method comprising providing therapeutic gas at a first pressure at a device end of a positive airway pressure mask, the first pressure higher than a prescribed pressure for the patient such that therapeutic gas pressure at a patient end of the mask is substantially the same as the prescribed pressure.

Other exemplary embodiments may be a system comprising a source of therapeutic gas under pressure, and a positive airway pressure mask having a device end and a patient end, the device end coupled to the source of therapeutic gas, and the patient end coupled to an airway of the patient. The system compensates for resistance to gas flow of the mask by increasing the pressure of the therapeutic gas at the device end of the mask above the patient's prescribed titration pressure.

Yet further exemplary embodiments may be a respiratory mask comprising a first nostril interface operable to substantially seal to a first nostril of a patient, a second nostril interface operable to substantially seal to a second nostril of the patient, an oral mask operable to substantially seal to the mouth of the patient, a first supply tube that penetrates the oral mask and fluidly couples to the first nostril interface (the first supply tube is operable to fluidly couple to a first supply port of a positive airway pressure device), a second supply tube that penetrates the oral mask and fluidly couples to the second nostril interface (the second supply tube is operable to fluidly couple to a second supply port of the positive airway pressure device), and a third supply tube fluidly coupled to the oral mask (the third supply tube operable to fluidly couple to a third supply port of the positive airway pressure device).

Other exemplary embodiments may be a respiratory mask comprising a first nostril interface operable to substantially seal to a first nostril of a patient, a second nostril interface operable to substantially seal to a second nostril of the patient, a first supply tube fluidly coupled to the first nostril interface, the first supply tube is operable to fluidly couple to a first supply port of a positive airway pressure device, and a second supply tube fluidly coupled to the second nostril interface, the second supply tube is operable to fluidly couple to a second supply port of the positive airway pressure device.

The disclosed devices and methods comprise a combination of features and advantages which enable it to overcome the deficiencies of the prior art devices. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct connection. Thus, if a first device couples to a second device, that connection may be through a direct connection, or through an indirect connection via other devices and connections.

Further, use of the terms "pressure," "applying a pressure," and the like shall be in reference herein, and in the claims, to gauge pressure rather than absolute pressure. Thus, application of a negative pressure shall mean a pressure below atmospheric.

DETAILED DESCRIPTION OF THE PREFERRED EMBODIMENTS

Figure 1:
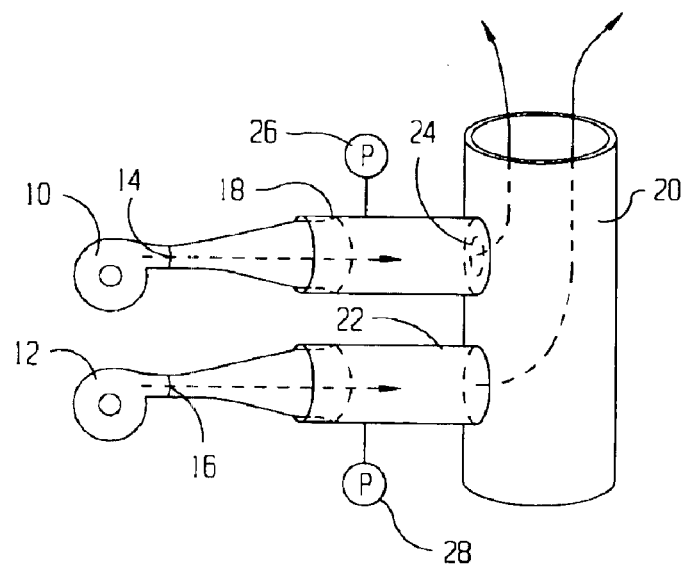
FIG. 1 shows an exemplary system for explanation of the relationship of pressure, flow and resistance to flow.

Consider, for purposes of explanation of the relationship between pressure and air flow, the system illustrated in FIG. 1. FIG. 1 illustrates a first fan or blower 10 and a second fan or blower 12. The blowers 10, 12 may be capable of providing controllable flows and/or controllable pressures on their outlet ports 14, 16 respectively. Blower 10 may have its outlet port 14 fluidly coupled to tube 18, and tube 18 may be fluidly coupled to a common chamber 20. Likewise, blower 12 may be fluidly coupled to a tube 22, and the tube 22 may likewise be coupled to the common chamber 20. In the illustration of FIG. 1, tube 18 may fluidly couple to chamber 20 through an orifice 24, and tube 22 may fluidly couple to the common chamber 20 without an orifice (or an orifice having a flow path significantly larger than that of orifice 24). Thus, while each tube 18 and 22 may be fluidly coupled to the common chamber 20, there is a restriction or resistance to air flow from the tube 18 into the chamber 20 by virtue of the orifice 24.

Further consider that each tube 18, 22 has coupled thereto a pressure transducer 26, 28 respectively. The pressure transducers are for purposes of illustration, and may not be required in some embodiments of the invention. Each of the pressure transducers 26, 28 may be capable of reading a pressure within the respective tube 18, 22. Blowers 10, 12 may be operated in a pressure control mode. While the controlled pressure within each tube may be different, for purposes of explanation consider that the pressure within each tube 18, 22 are controlled to be the same. Further consider that the common chamber 20 is at a low pressure, such as vented to atmosphere. Thus, because of the pressure differentials between the tubes 18, 22 and the common chamber 20, there may be an airflow from the tubes 18, 22 into the chamber 20 (as indicated by the arrows in FIG. 1). However, in spite of the fact that the pressure within the tubes 18, 22 may be the same in this example, the air flow may be different. That is, orifice 24 may provide a resistance to air flow from the tube 18 into the common chamber 20 that is not experienced by air flow moving through tube 22. In particular, because of the restriction caused by orifice 24, the air flow through tube 18 may be less than the air flow through tube 22. Thus, even for the same pressure within the tubes 18, 22, the air flow through those tubes may be different.

Now consider that the blowers 10, 12 are operated in a flow control mode, with each blower attempting to maintain equivalent air flow regardless of required pressure. In order to maintain the desired flow, blower 10 may need to develop a higher pressure to overcome the restriction of orifice 24 than the pressure that may be required of blower 12 for the same flow. With these principles in mind, the specification now turns to a discussion of the method and related systems for providing positive airway pressure to a patient.

Figure 2:
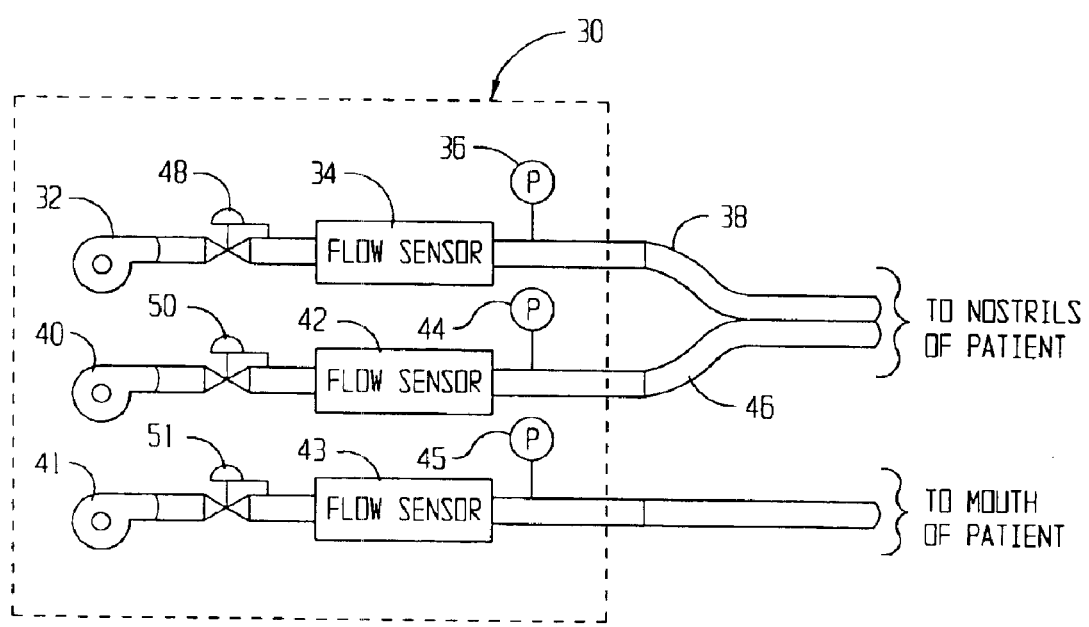
FIG. 2 shows a positive airway pressure device constructed in accordance with at least some embodiments of the invention.

FIG. 2 illustrates a machine or device 30 for providing positive airway pressure in accordance with some embodiments of the invention. A device 30 constructed in accordance with embodiments of the invention preferably has the capability of individually controlling pressure and/or therapeutic gas flow to each nostril or naris of the patient, and in some embodiments to the patient's mouth. This is in contrast to related art CPAP devices which do not differentiate as to the amount of flow into each naris. Thus, a first flow path may comprise a blower 32 fluidly coupled to a flow sensor 34 and pressure transducer 36. Blower 32 may be any suitable device, such as a vane-type blower coupled to an electric motor. In alternative embodiments, a source of therapeutic gas, e.g. oxygen, may be used in addition to or in combination with the blower 32. Therapeutic gas pressure and flow created by the blower 32 may thus flow through the flow sensor 34 (of any suitable type) and to a first naris of a patient, possibly through tube 38. The positive airway pressure device 30 in accordance with embodiments of the invention may also comprise a second blower 40 coupled to a second flow sensor 42 and second pressure transducer 44. The blower 40 may be of similar design and construction to that of blower 32. In alternative embodiments, the blower 40 may be used in combination with or replaced by a source of compressed therapeutic gas, e.g. oxygen. Therapeutic gas pressure and flow created by blower 40 may thus flow through the flow sensor 42 (of any suitable type) and to a second naris of the patient, possibly through tube 46. Before proceeding, it should be understood that while the exemplary embodiments illustrated in FIG. 2 have both a pressure transducer and a flow sensor in each flow path, having both these devices is not strictly required. Some embodiments may operate with only a flow sensor or only a pressure transducer in each flow path.

In accordance with embodiments of the invention, the positive airway pressure device 30 controls pressure and/or flow to each naris of a patient individually. In some embodiments, therapeutic gas flow to the patient may be divided among the nares so as not to force any one naris to carry all the therapeutic gas flow. In order to ensure that each naris is carrying at least part of the therapeutic gas flow, the flow path for each naris may need individual pressure and/or flow control. In alternative embodiments, the therapeutic gas flow through each naris may be individually controlled to be different.

Control of the pressure, and therefore the therapeutic gas flow may take many forms. In one embodiment, the pressure may be controlled by selectively controlling blower speed, e.g. by controlling the speed of the motor coupled to the blower. In alternative embodiments, the blowers 32, 40 may be operated at a constant speed and the pressure provided to the patient may be controlled by pressure control valves 48, 50 for the blowers 32, 40 respectively. In yet other embodiments, a combination of controlling the blower speed in a pressure control valve may be utilized.

Figure 3:
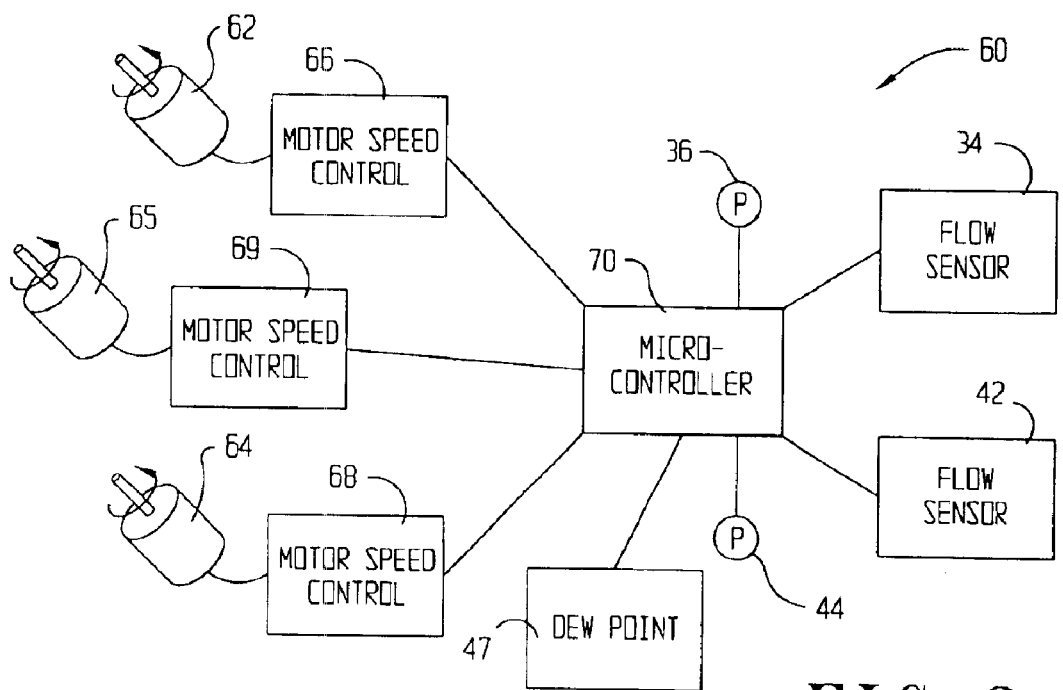
FIG. 3 shows a control system in accordance with at least some embodiments of the invention.

FIG. 3 illustrates a control system 60 which may be used to control the positive airway pressure device as illustrated in FIG. 2. In particular, coupled to each of the blowers 32, 40 may be a motor 62, 64 respectively. The speed of the output shaft of each motor 62, 64 (and therefore the blower speed) may be controlled by a motor speed control unit 66 and 68 respectively. In at least some embodiments, the motors 62, 64 may be DC motors, whose speed may be controlled by varying the applied DC voltages. In alternative embodiments, voltage to each of the motors 62, 64 may remain constant, but may be modulated, such as by pulse width modulation control. In yet other embodiments of the invention, the motors 62, 64 may be AC motors, and in these embodiments the motor speed control circuit 66, 68 may provide control voltages having varying voltages and frequencies to the motors so as to control motor speed.

The control system 60 also may comprise a microcontroller 70 coupled to the motor speed control circuit 66 and 68. The microcontroller 70 may be any suitable microcontroller or microprocessor programmed to provide an indication to each of the motor speed control circuits 66 and 68 of a desired motor speed. Determining a motor speed may be based, in some embodiments, on pressures read by the microcontroller 70 from the pressure transducers 36 and 44. In other embodiments, the desired motor speeds may be set based on gas flows measured by the flow sensors 34 and 42. In these flow control embodiments, pressure transducers may not be required. Although microprocessor control is preferred, the positive airway pressure device may be equivalently implemented with an analog control system.

In accordance with some embodiments of the invention, the microcontroller 70 may be provided with a prescribed titration pressure, possibly by way of a dial-type input (not shown) or some other form of user interface (not shown). Based on the prescribed pressure, the microcontroller may ramp the speed control signal passed to each of the motor speed control circuits 66 and 68 to achieve the desired pressure. If a naris is severely congested or otherwise blocked (e.g. by a tumor or polyp), however, therapeutic gas flow may move only through an open naris at the prescribed titration pressure. Moreover, throughout the night, the restriction or resistance to flow experienced within each naris may change, e.g. as a function of congestion experienced within each naris or as a function of an amount of swelling of the soft tissue within each naris. Thus, even at the prescribed pressure the patient may receive inadequate therapeutic gas. A positive airway pressure device in accordance with embodiments of the invention may measure the therapeutic gas flow through each naris, possibly by reading signals from the flow sensors 34 and 42. If the therapeutic gas flow to the nares is at least partially evenly divided among the nares, no further action may be required other than to control pressure. If, however, the measured flow is not at least partially balanced, some embodiments of the device 30 may attempt to equalize the flow by changing the pressure applied to one naris.

A positive airway pressure device in accordance with embodiments of the invention may at least momentarily increase the pressure to the blocked or partially blocked naris in an attempt to establish a flow. Once established, the flow of therapeutic gas through the naris may act as a pneumatic splint (in the much the same way that the flow may act to splint the larynx to reduce the hypopnea and apnea events), and therefore the applies pressure may be reduced after opening.

Figure 4:
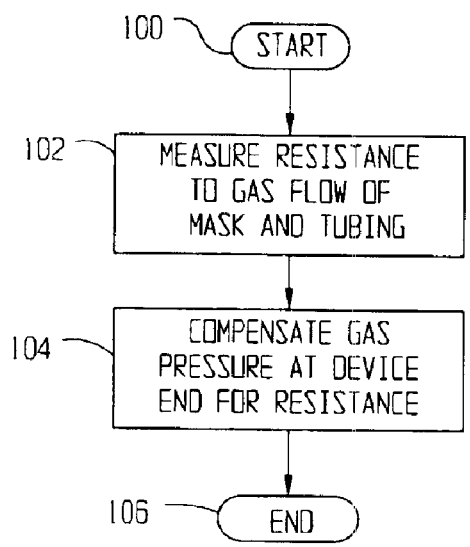
FIG. 4 shows an exemplary method in accordance with embodiments of the invention.

Alternative embodiments may be concerned with the prescribed titration pressure. In particular, a doctor may prescribe a certain pressure found to achieve the desired results in a patient. However the inventors of the current specification have found that the masks, and related tubing, used to provide continuous positive airway pressure in the related art have a resistance to the flow of therapeutic gas (e.g. air or oxygen enriched air). This resistance to flow results in a pressure drop across the mask and tubing such that the patient may not be provided the desired titration pressure at the mask. FIG. 4 illustrates a method that may be implemented in accordance with at least some embodiments of the invention that address this deficiency of the related art. In particular, the process may start (block 100) and proceed to a determination of the resistance to gas flow of the mask and related tubing (block 102). In accordance with some embodiments of the invention, this determination may be made prior to the patient placing the mask against the patient's airways for use. In accordance with at least some embodiments, determining the resistance to air flow of the mask and related tubing may be accomplished by applying a known pressure at a positive airway pressure device end of the mask and tubing and measuring the flow of gas through the tube. Using these two parameters, and taking into account the controlled leak proximate to the patient's airways (discussed more fully below), a value of the resistance of the mask and tubing may be calculated. Once the resistance to gas flow of the mask and tubing is determined, the patient may couple the mask to the breathing airways and pressure application may begin. However, in accordance with these embodiments the pressure applied by the positive airway pressure device may be greater than the titration pressure prescribed by the doctor, and the amount that the pressure is above the prescribed pressure may thus compensate for pressure drop across the mask and tubing (block 104) such that the pressure experienced proximate to the patient's airways is substantially the same as the prescribed pressure. Thereafter, the process may end (block 106).

Notwithstanding the calculation of resistance to airflow prior to application of the prescribed pressure to the patient's airways, at least some embodiments of the invention may also adjust the pressure supplied at the device end to compensate for resistance to airflow changes during use. In particular, the relative humidity (related to dew point) of the therapeutic gas moving through the tubing and respiratory mask affects the resistance to flow experienced by the gas. The higher the relative humidity, the higher the resistance to flow experienced by the gas. Thus, embodiments of the invention monitor relative humidity of the supplied therapeutic gas, and as the relative humidity changes the pressure applied by the device 30 may likewise change to ensure the pressure provided within the patient's airway during inhalation is substantially the titration pressure prescribed. FIG. 3 illustrates a dew point monitor 47 coupled to the microcontroller 70. The microcontroller 70 may periodically read the dew point monitory 47, and adjust the applied pressure at the device 30 to compensate for changes in resistance to flow through the tubing and respiratory mask. While any dew point or relative humidity sensor may be used, the preferred sensor is a solid state relative humidity sensor manufactured by Honeywell having a part no. HIH-3602-C.

In yet further alternative embodiments, medical doctors may prescribe a total therapeutic gas flow rather than a titration pressure. In these circumstances, the positive airway pressure device 30, possibly using the control system illustrated in FIG. 3, may attempt to substantially evenly distribute the flow through each naris such that the total prescribed therapeutic flow is achieved. In these alternative embodiments, the control system 60 may monitor only flow signals produced by the flow sensors 34, 42. It may be in these circumstances that once flow is established in the nares, the applied pressures may be substantially equal; however, in controlling flow differing pressures within each naris may be required. In yet further alternative embodiments, medical doctors may prescribe a therapeutic gas flow for each naris individually, and in these circumstances the positive airway pressure device 30 may distribute the flow through each naris according to the prescription. In order to achieve these differing flows, the positive airway pressure device 30 may apply substantially different pressures to each naris.

Dividing the air flow substantially evenly between the nares may be more comfortable for the patient. A device that is capable of adjusting its pressure to ensure airflow may more accurately provide that airflow in spite of the fact that the resistance to flow through a naris may change significantly over the course of a night. Further, dividing the therapeutic gas flow among the nares substantially evenly may reduce discomfort associated with drying of the nasal cavities by the air flow through the nares (in comparison to forcing the air flow through a single naris).

Embodiments of the invention may not, however, increase pressure indefinitely in an attempt to evenly distribute the air flow across the nares. In particular, the microcontroller 70 may have an upper limit of pressure, for example 20 cm $H_2O$, that it may apply to a particular naris in an attempt to open the naris or provide a desired air flow. If therapeutic gas flow has not been established or the naris has not been opened upon reaching an upper limit pressure, the microcontroller 70 may resort to providing the necessary therapeutic gas flow to the open naris, and possibly reporting the blockage by means of a user interface (not shown). In yet further embodiments, discussed below, the microcontroller 70 may augment the pressure and/or flow provided to the only open naris of a patient with delivery of therapeutic gas to the patient's mouth. If over the course of a treatment (for example overnight) the formerly clogged naris becomes less resistant to therapeutic gas flow, the microcontroller may begin providing gas flow at that point.

In yet other alternative embodiments, the positive airway pressure device 60 may be coupled to the patient's nares, but may initially refrain from providing pressure and/or flow. Thus, in an initial state the positive airway pressure device 60 may merely monitor flow through the nares, and become operational only if a disruption in flow occurs. For example, if the patient changes sleeping position an obstruction may arise, and in this case the device 60 may activate one or more blowers to apply airway pressure and/or ensure therapeutic gas flow. As yet another example, the patient may develop a congestion in one or both nares, and upon detecting the blockage in the form of congestion the device 60 may activate one or more blowers to apply airway pressure and/or ensure therapeutic gas flow. In another example, the device 60 may monitor flow through the nares, and upon detecting the patient is snoring (e.g. by detecting rapid undulations in the measure flow) may activate one or more blowers to apply airway pressure and/or ensure therapeutic gas flow. In yet other embodiments, the device 60 may initially provide the patient air filtered for allergens, and may provide therapeutic gas at some later time, if required.

Referring again to FIG. 2, the discussion to this point has focused solely on individually controlling the pressure and/or therapeutic gas flow to the nares of a patient. However, in accordance with at least some embodiments, in addition to providing positive airway pressure to the nares, a positive airway pressure may also be provided to the mouth of the patient. Thus, FIG. 2 illustrates a blower 41 connected to the mouth of the patient, possibly through a flow sensor 43. Much like blowers 32 and 40, the speed of blower 41 may be controlled to selectively control one or both of the pressure applied to the mouth of the patient or the flow through the mouth of the patient. In alternative embodiments, valve 51 may be used to control the pressure and/or flow, possibly with blower 41 operating at a constant speed. FIG. 2 also illustrates that a pressure transducer 45 may also be used in the flow circuit to the patient's mouth. Likewise, FIG. 3 illustrates a motor 65 coupled to a motor speed control circuit 69 and microcontroller 70. Thus, the discussion with respect to controlling speed of blowers 32 and 40 is likewise applicable to blower 41.

Thus, in accordance with these alternative embodiments the therapeutic gas flow and/or pressure to each of the patient's nostrils and mouth may be individually controlled. In these embodiments, positive airway pressure may be applied to the nostrils only, to the mouth only, or to a combination of one or more nostrils and the mouth depending on the particular situation of the patient. Consider, for example, a patient being provided positive airway pressure during inhalation only to the nostrils. As one nostril becomes congested, the positive airway pressure device 30 may be unable to provide sufficient flow through the remaining nostril or naris to prevent apnea or hypopnea events. In this case, in accordance with embodiments of the invention, additional positive airway pressure may be provided to the patient by way of the mouth. Relatedly, a physical abnormality, tumor or polyp may permanently block air flow through one nostril of a patient, and thus positive airway pressure may be supplied to the patient through the open nostril as well as the mouth.

Applying positive airway pressure individually through the nostrils assumes that the patient does not mouth breathe. In some cases, however, patients (especially during sleep) may transition between nasal only breathing and a combination nasal and mouth breathing. For those patients operating under a titration pressure, opening of the mouth increases flow through one or more of the nostrils as part of the gas escapes through the mouth, even during an inhalation. This increase in flow may likewise increase the nasal irritation associated with that flow. Moreover, the escape of the therapeutic gas through the mouth may mean that insufficient therapeutic gas reaches the lungs (apart from the benefits of the positive airway pressure). In accordance with alternative embodiments of the invention, initially the blower 41 may be turned off and the flow sensor 43 may be coupled to the mouth of the patient. During periods of time when the patient's mouth is closed, the positive airway pressure device 30 may selectively control therapeutic gas pressure and/or flow using the blowers 32, 40 and related devices. When the patient opens the mouth and begins to mouth breathe, the positive airway pressure device 30 may take corrective action. In some embodiments, the positive airway pressure device 30 may activate blower 41 to supply therapeutic gas to the mouth at a particular pressure. In these embodiments, the positive airway pressure device 30 may attempt to provide a pneumatic block to airflow through the mouth. In yet further embodiments, upon detecting mouth breathing the positive airway pressure device may provide the flow of therapeutic gas and/or pressure to the patient at least partially through the open mouth.

The embodiments discussed to this point have been in relation to providing positive airway pressure to a patient during inhalation. Related art continuous airway pressure (CPAP) devices provide the positive airway pressure even during exhalation. However, in accordance with at least some embodiments of the invention the positive airway pressure device 30 reduces the pressure within the patient's airways to ease the patient effort required to exhale. The reduction in airway pressure may take many forms. In some embodiments, the airway pressure may be reduced yet the pressure within the airways may still be above atmospheric or ambient pressure. In yet other embodiments, the application of pressure may be removed entirely such that the airways experience substantially atmospheric pressure during the exhalation process. In yet further embodiments, a negative pressure (vacuum) may be applied to assist the patient with the exhalation process. Referring again to FIG. 2, in embodiments where the pressure is reduced, yet still above atmospheric, one or more of the blowers 32, 40, 41 may slow such that the pressure of the therapeutic gas at the patient is reduced yet still be above atmospheric pressure. In accordance with embodiments where application of airway pressure is ceased, one or more of the blowers 32, 40, 41 may stop operation completely during the exhalation process. In accordance with embodiments where a negative pressure is applied to the patient's airways, one or more of the blowers 32, 40, 41 may turn in the direction opposite of that where a pressure is applied, thus assisting the patient's exhalation through the attached airway. Inasmuch as the nostrils and mouth of the patient may each have their own pressure and flow control circuit, each of the nostrils and mouth may be individually controlled such that one or more of these breathing airways has a reduced or negative pressure applied, while the others may remain unchanged or may be controlled at different pressures.

Figure 5:
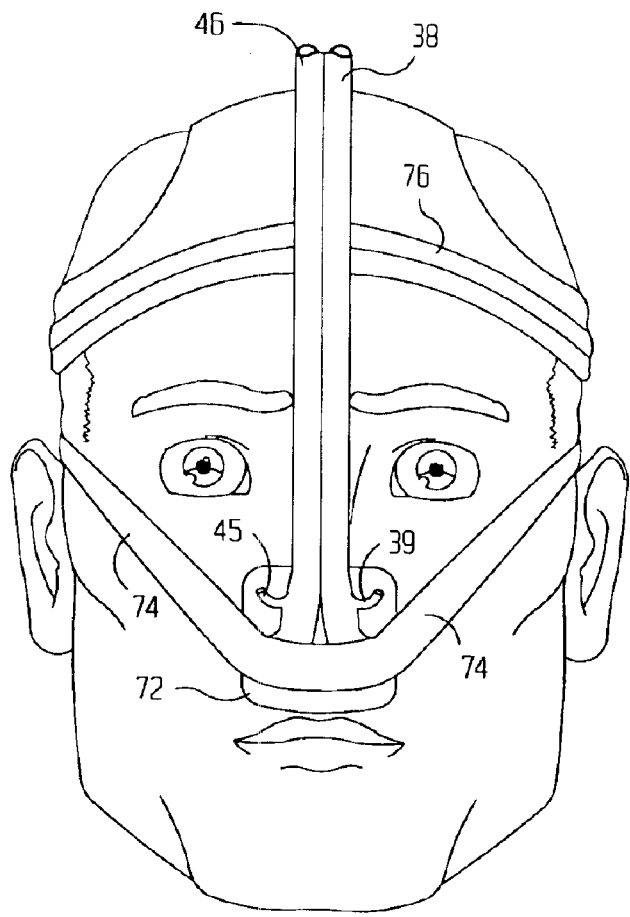
FIG. 5 shows a respirator mask in accordance with at least some embodiments of the invention.

Referring again briefly to FIG. 2, the tubes 38, 46 are disclosed to couple to the nostrils of the patient. FIG. 5 illustrates embodiments of a respiratory mask for coupling each of the tubes 38, 46 to the nares of the patient. In particular, the mask may comprise a nose portion 72 which fluidly couples the delivery tube 38 to a first naris (in this case the left naris) and fluidly couples the delivery tube 46 to a second naris (in this case the right naris). The nose portion 72 may be held in place by a strap 74. Strap 76 may act to hold the delivery tubes 38 and 46 in the relative position shown, extending over the forehead. The nose portion 72 may seal to each nostril by sealing surface contacting an outer portion of each naris. In alternative embodiments, the nose portion may comprise tubular members which extend a some distance into each naris, thus forming a seal with the internal portions of the naris. Each of the tubes 38, 46 preferably has a controlled vent 39, 45 respectively as shown in FIG. 5. The vents 39, 45 may allow exhaled gasses to escape to atmosphere during the exhalation process. In embodiments of the invention where the positive airway pressure device controls the flow of therapeutic gas into each nostril, the amount of therapeutic gas escaping through each of the vents 39 and 40 may be taken into account.

Figure 6:
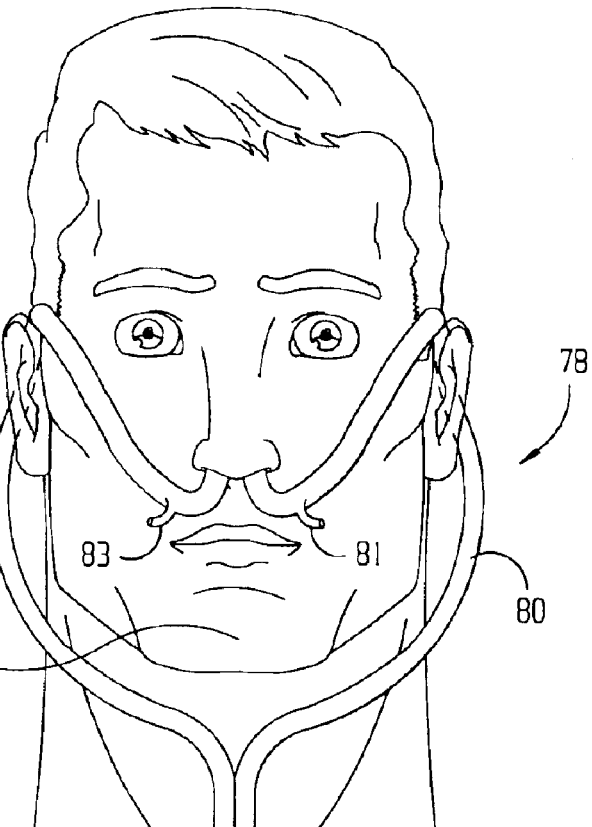
FIG. 6 shows a respirator mask in accordance with at least some embodiments of the invention, that may be used with a positive airway pressure device in accordance with embodiments of the invention.
Figure 7:
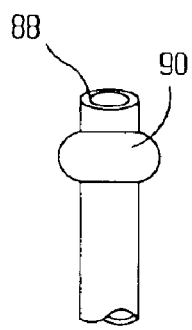
FIG. 7 shows a sealing surface for one tube of a respirator mask in accordance with at least some embodiments of the invention.
Figure 8:
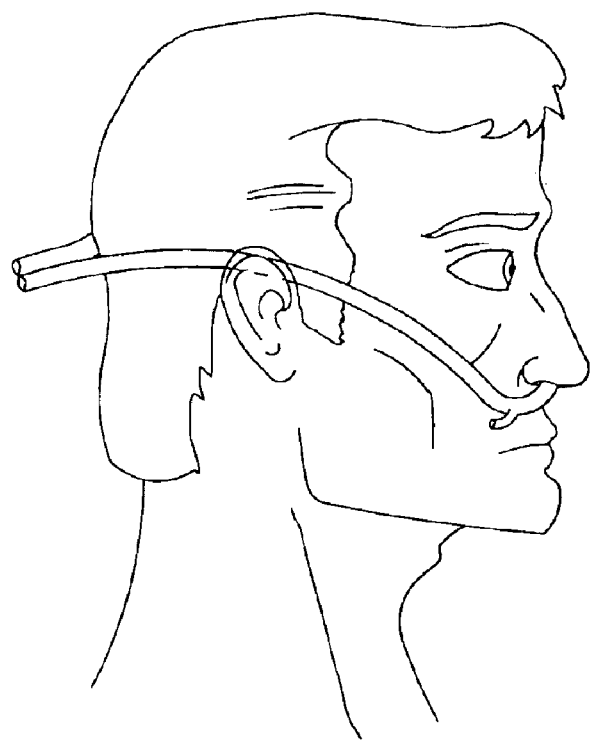
FIG. 8 shows an alternative convergence point for the respirator mask of FIG. 6.

FIG. 6 illustrates alternative embodiments of a respiratory mask that may be used in accordance with embodiments of the invention. In particular, the mask 78 may comprise a first supply tube 80 (which may be the same as supply tube 38 or 46) and a second supply tube 82 (which may be the same as supply tube 38 or 46). In accordance with embodiments of the invention, the supply tubes 80 and 82 are not in fluid communication with each other. Distal end 84 of tube 80 may couple to a first flow path of a positive airway pressure device, such as device 30. Likewise, distal end of 86 of tube 82 may couple to a second flow path of a positive airway pressure device, such as pressure device 60 (not shown in FIG. 6). Each tube 80 and 82 may seal, or substantially seal, on a second end to a naris of the patient, and likewise each tube may have a respective vent 81, 83. The seal may be to an outer surface of each naris, but preferably the tubes seal to an inner surface of each naris. FIG. 7 illustrates an exemplary end 88, which could be of either tube 80 and/or 82, comprising a seal 90 designed to snugly fit on an inside diameter of a naris. Returning again to FIG. 6, the tubes 80, 82 may converge, in some embodiments, below the chin of the patient. In alternative embodiments, the tubes 80, 82 may converge behind the patient's head, as illustrated in FIG. 8. Convergence behind the head may be more comfortable for patients that sleep on their sides.

Figure 9:
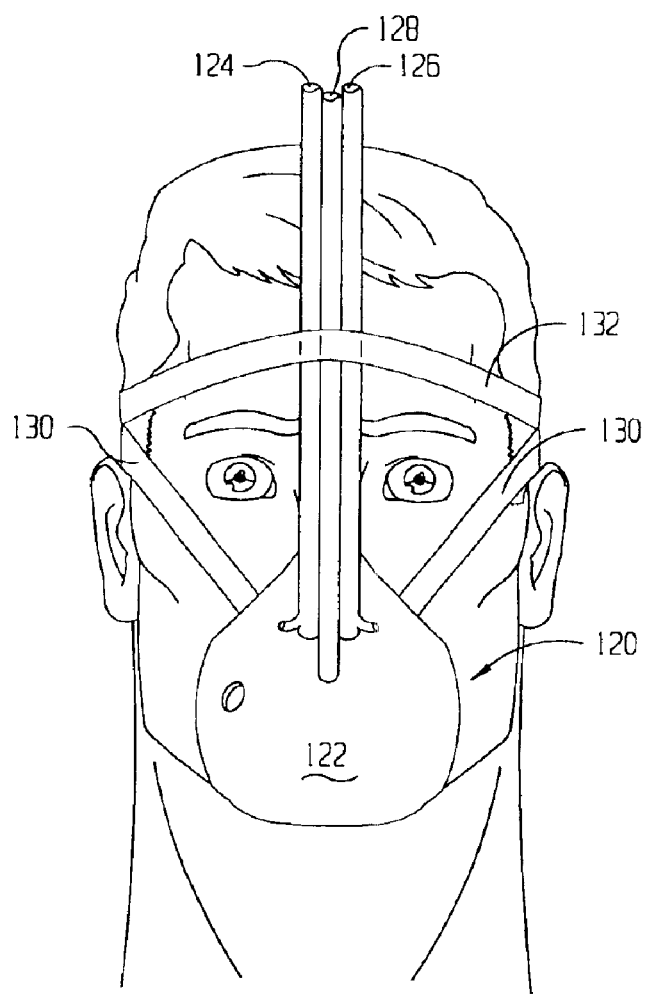
FIG. 9 shows a respiratory mask in accordance with alternative embodiments of the invention.

The respiratory masks of FIGS. 5, 6 and 8 may be operable in embodiments that control therapeutic gas pressure and/or flow into the nostrils only. FIG. 9 illustrates a respiratory mask that may be used in accordance with embodiments of the invention that individually control the therapeutic gas pressure and/or flow into both the nostrils and the mouth of the patient. In particular, FIG. 9 shows a respiratory mask 120 comprising a oral mask portion 122 that covers both the nose and mouth. Supply tubes 124 and 126 fluidly coupled to the nostrils or nares of the patient. Supply tube 128 penetrates the oral mask 122 and is fluidly connected to the volume within the oral mask 122. The oral mask 122 may be held in place by straps 130, and the supply tubes 124, 126 and 128 may be held in place by strap 132.

Figure 10:
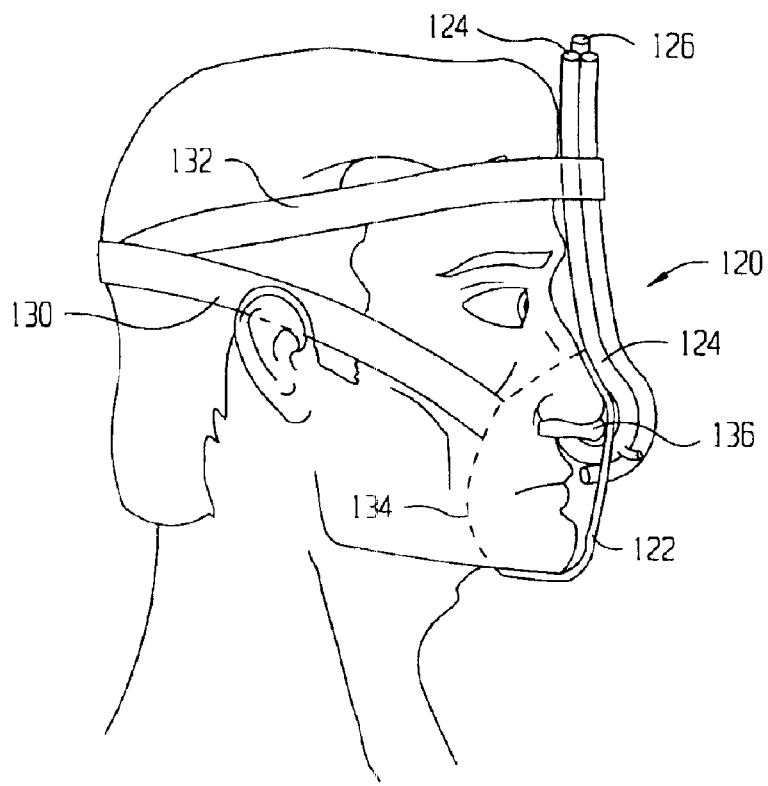
FIG. 10 shows a partial cross-sectional side view of the respiratory mask of FIG. 9 in accordance with embodiments of the invention.
Figure 11:
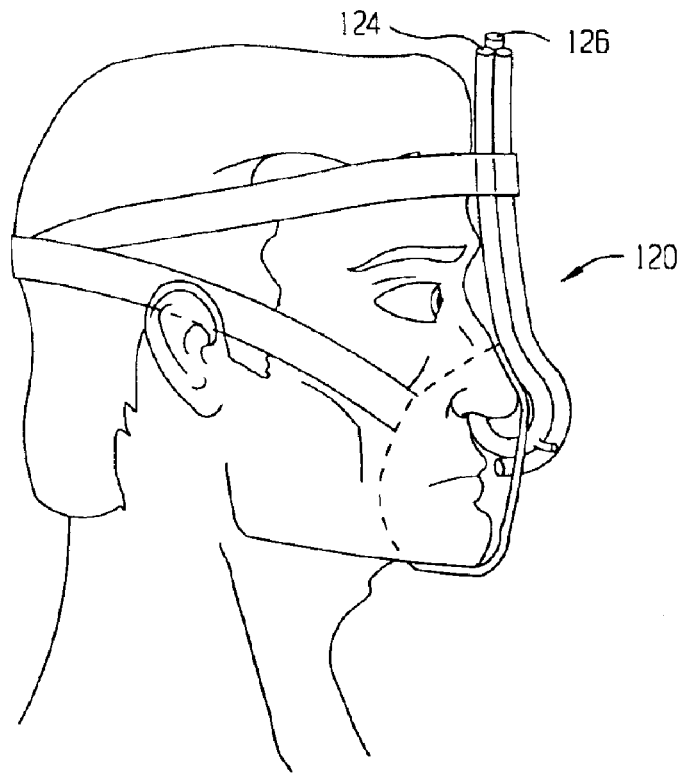
FIG. 11 shows a partial cross-sectional side view of the respiratory mask of FIG. 9 in accordance with alternative embodiments of the invention.

FIG. 10 shows a cross-sectional side view of the respiratory mask 120. In the embodiments illustrated in FIG. 10, the oral mask 122 is shown to seal against the patient's face at the nose, under the chin, and along dashed line 134. In the embodiments illustrated in FIG. 10, the sensing tube 124 sealingly couples to the patient's right nostril by way of a sealing pillow 136. The left nostril of the patient, which is not visible in FIG. 10, would likewise utilize a sealing pillow between the sensing tube 126 and the left naris. FIG. 11 illustrates alternative embodiments of the invention, in a view similar to that of FIG. 10, except that the supply tube 124 extends a short distance into the nare and seals against the inner surface.

Though the masks illustrated in the figures may be preferred, any mechanism by which the delivery tubes are fluidly coupled to their respective naris may be used without departing form the scope and spirit of the invention.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method comprising:
    applying therapeutic gas pressure within a first naris of a patient during respiration; and
    applying therapeutic gas pressure within a second naris of the patient during the respiration;
    wherein the therapeutic gas pressures applied to each naris are different.

2. The method as defined in claim 1 further comprising:
    applying positive therapeutic gas pressure within the first naris during an inhalation; and
    applying positive therapeutic gas pressure within the second naris during the inhalation.

3. The method as defined in claim 2 further comprising controlling the therapeutic gas pressure within each naris such that the therapeutic gas flow through each naris is substantially the same.

4. The method as defined in claim 2 further comprising controlling the therapeutic gas pressure within each naris such that the therapeutic gas flow through each naris is different.

5. The method as defined in claim 2 further comprising reducing the therapeutic gas pressure within the first naris during an exhalation.

6. The method as defined in claim 5 further comprising reducing therapeutic gas pressure within the second naris during the exhalation.

7. The method as defined in claim 5 wherein reducing the therapeutic gas pressure within the first naris during the exhalation further comprises removing the positive therapeutic gas pressure during the exhalation.

8. The method as defined in claim 5 wherein reducing the therapeutic gas pressure within the first naris during the exhalation further comprises applying a negative pressure within the first naris.

9. The method as defined in claim 1 further comprising:
    reducing pressure within the first naris during an exhalation, the reducing with respect to therapeutic gas pressure applied during inhalation; and
    reducing pressure within the second naris during an exhalation, the reducing with respect to therapeutic gas pressure applied during inhalation.

10. The method as defined in claim 9 wherein reducing pressure within the first naris further comprises removing positive therapeutic gas pressure applied during inhalation.

11. The method as defined in claim 9 further comprising applying a negative pressure to the first naris.

12. A system comprising:
    a first blower having an outlet port fluidly coupled to a first pressure transducer, wherein the first blower operatively couples to a first naris of a patient; and
    a second blower having an outlet port fluidly coupled to a second pressure transducer, wherein the second blower operatively couples to a second naris of the patient.

13. The system as defined in claim 12 further comprising:
    wherein the first blower controls therapeutic gas pressure within the first naris during an inhalation of the patient; and
    wherein the second blower controls therapeutic gas pressure within the second naris during the inhalation of the patient.

14. The system as defined in claim 13 wherein the pressure controlled within the first naris is different than the pressure controlled within the second naris.

15. The system as defined in claim 13 wherein the pressure controlled within the first naris is substantially the same as the pressure controlled within the second naris.

16. The system as defined in claim 13 further comprising:
    wherein the first blower applies a positive therapeutic gas pressure within the first naris to achieve a therapeutic gas flow through the first naris;
    wherein the second blower applies a positive therapeutic gas pressure within the second naris to achieve a therapeutic gas flow through the second naris; and
    wherein the therapeutic gas flow through the first and second naris is substantially the same.

17. The system as defined in claim 13 further comprising:
    wherein the first blower applies a positive therapeutic gas pressure within the first naris to achieve a therapeutic gas flow through the first naris;
    wherein the second blower applies a positive therapeutic gas pressure within the second naris to achieve a therapeutic gas flow through the second naris; and
    wherein the therapeutic gas flow through the first and second naris is different.

18. The system as defined in claim 13 wherein the first blower reduces therapeutic gas pressure within the first naris during an exhalation of the patient.

19. The system as defined in claim 18 wherein the first blower removes the therapeutic gas pressure during the exhalation.

20. The system as defined in claim 18 wherein the first blower applies a negative pressure within the first naris during the exhalation.

21. The system as defined in claim 12 wherein the first blower reduces pressure within the first naris during an exhalation, the reduction in pressure with respect to pressure within the first naris during an inhalation.

22. The system as defined in claim 21 wherein the second blower reduces pressure within the second naris during an exhalation, the reduction in pressure with respect to pressure within the second naris during an inhalation.

23. The system as defined in claim 21 wherein the first blower applies a negative pressure within the first naris during the exhalation.

24. A method comprising:
   applying a therapeutic gas flow into a first naris of a patient during an inhalation, the therapeutic gas flow comprising substantially all the gas inspired through the first naris during the inhalation; and
   applying a therapeutic gas flow into a second naris of a patient during the inhalation, the therapeutic gas flow comprising substantially all the gas inspired through the second naris during the inhalation;
   wherein the therapeutic gas flow into each naris is achieved by differing applied pressures within each naris.

25. The method as defined in claim 24 wherein the therapeutic gas flow into the first naris is different than the therapeutic gas flow into the second naris.

26. The method as defined in claim 24 wherein the therapeutic gas flow into the first naris is substantially the same as the therapeutic gas flow into the second naris.

27. The method as defined in claim 24 further comprising:
   forcing gas flow out of the first naris during an exhalation; and
   forcing gas flow out of the second naris during the exhalation.

28. The method as defined in claim 27 wherein the therapeutic gas flow out of the first naris during the exhalation is different than the therapeutic gas flow out of the second naris during the exhalation.

29. The method as defined in claim 27 wherein the therapeutic gas flow out of the first naris during the exhalation is substantially the same as the therapeutic gas flow out of the second naris during the exhalation.

30. The method as defined in claim 24 further comprising ceasing the control of gas flow of the first naris during an exhalation.

31. A system comprising:
   a first blower fluidly coupled to an outlet port through a first flow sensor, wherein the first blower and first flow sensor operatively couple to a first naris of a patient and provide substantially all the gas inspired through the first naris during an inhalation; and
   a second blower fluidly coupled to an outlet port through a second flow sensor, wherein the second blower and second flow sensor operatively couple to a second naris of the patient and provide substantially all the gas inspired through the second naris during the inhalation;
   wherein a pressure applied by the first blower to the first naris to achieve a desired gas flow is different that a pressure applied by the second blower to the second naris to achieve a desired gas flow.

32. The system as defined in claim 31 wherein gas flow into the first naris during the inhalation is substantially the same as the gas flow into the second naris during the inhalation.

33. The system as defined in claim 31 wherein gas flow into the first naris during the inhalation is different than the therapeutic gas flow into the second naris during the inhalation.

34. A system comprising:
   a first blower fluidly coupled to an outlet port, wherein the first blower operatively couples to a first naris of a patient and provides substantially all the gas inspired through the first naris during an inhalation; and
   a second blower fluidly coupled to an outlet port, wherein the second blower operatively couples to a mouth of the patient and provides substantially all the gas inspired through the mouth during the inhalation.

35. The system as defined in claim 34 wherein the second blower provides gas pressure to the mouth to act as at least a partial pneumatic blockage to reduce the amount of gas escaping through the mouth provided to the first naris during the inhalation of the patient.

36. The system as defined in claim 34 further comprising:
   a third blower fluidly coupled to an outlet port, wherein the third blower operatively couples to a second naris of a patient and provides substantially all the gas inspired through the second naris during the inhalation; and
   wherein a pressure applied by the first blower to the first naris to achieve a desired gas flow is different that a pressure applied by the third blower to the second naris to achieve a desired gas flow.

37. The system as defined in claim 36 wherein the second blower provides gas pressure to the mouth to act as at least a partial pneumatic blockage to reduce the amount of gas escaping through the mouth provided to the first and second naris during the inhalation of the patient.

38. A respiratory mask for delivery of positive airway pressure comprising:
   a first nostril interface operable to substantially seal to a first nostril of a patient;
   a second nostril interface operable to substantially seal to a second nostril of the patient;
   an oral mask operable to substantially seal to the mouth of the patient;
   a first supply tube that penetrates the oral mask and fluidly couples to the first nostril interface, the first supply tube is operable to fluidly couple to a first supply port of a positive airway pressure device;
   a second supply tube that penetrates the oral mask and fluidly couples to the second nostril interface, the second supply tube is operable to fluidly couple to a second supply port of the positive airway pressure device;
   a third supply tube fluidly coupled to the oral mask, the third supply tube operable to fluidly couple to a third supply port of the positive airway pressure device.

39. The respiratory mask as defined in claim 38 wherein the first, second and third supply tubes are operable to extend over a forehead of the patient when the respiratory mask is worn.

40. The respiratory mask as defined in claim 38 wherein the third supply tube is mechanically coupled to, and runs parallel with, the first supply tube.

41. The respiratory mask as defined in claim 38 wherein the first nostril interface extends into the first nostril of the patient, and seals against the inside diameter of the first nostril.

42. The respiratory mask as defined in claim 38 wherein the first nostril interface further comprises a sealing pillow that substantially seals against an exterior surface of the first nostril of the patient proximate to the first nostril.

43. The respiratory mask as defined in claim 38 wherein the oral mask seals over the patient's nose, wherein the first and second nostril interface are within a volume defined by the oral mask.

44. A respiratory mask for delivery of positive airway pressure comprising:

a first nostril interface operable to substantially seal to a first nostril of a patient;

a second nostril interface operable to substantially seal to a second nostril of the patient;

a first supply tube fluidly coupled to the first nostril interface, the first supply tube is operable to fluidly couple to a first supply port of a positive airway pressure device; and a second supply tube fluidly coupled to the second nostril interface, the second supply tube is operable to fluidly couple to a second supply port of the positive airway pressure device.

45. The respiratory mask as defined in claim 44 wherein the first and second supply tubes are operable to extend over a forehead of the patient when the respiratory mask is worn.

46. The respiratory mask as defined in claim 44 wherein the first and second supply tubes are operable to extend, one each, over ears of a patient.

47. The respiratory mask as defined in claim 46 wherein the first and second supply tubes converge below a chin of the patient.

48. The respiratory mask as defined in claim 46 wherein the first and second supply tubes converge at a back the head of the patient.

49. The respiratory mask as defined in claim 46 wherein the first nostril interface extends into the first nostril of the patient, and seals against the inside diameter of the first nostril.

50. The respiratory mask as defined in claim 46 wherein the first nostril interface further comprises a sealing pillow that substantially seals against an exterior surface of the first nostril of the patient proximate to the first nostril.

51. A system comprising:

a first blower fluidly coupled to a first outlet port, wherein the first blower is configured to couple to a first naris of a patient and provide substantially all the gas inspired through the first naris during an inhalation; and a second blower fluidly coupled to a second outlet port, wherein the second blower is configured to couple to a second naris of the patient and provide substantially all the gas inspired through the second naris during the inhalation.

52. The system as defined in claim 51 further comprising a flow sensor fluidly coupled between the first blower and the second outlet port.

53. The system as defined in claim 51 further comprising a pressure sensor fluidly coupled between an outlet of the first blower and the first outlet port.

54. The system as defined in claim 51 wherein a pressure applied by the first blower to the first naris to achieve a desired gas flow is different that a pressure applied by the second blower to the second naris to achieve a desired gas flow.

55. The system as defined in claim 51 wherein gas flow into the first naris during the inhalation is substantially the same as gas flow into the second naris during the inhalation.

56. The system as defined in claim 51 wherein gas flow into the first naris during the inhalation is different than the gas flow into the second naris during the inhalation.

* * * * *